United States Patent [19]
Vogler et al.

[11] Patent Number: 5,543,048
[45] Date of Patent: Aug. 6, 1996

[54] BLOOD COLLECTION ASSEMBLY WITH BLOOD COMPATIBLE, SHEAR SENSITIVE GELS

[75] Inventors: Erwin A. Vogler, Newhill; Thomas A. Shepard, Apex; Jane C. Graper, Durham, all of N.C.

[73] Assignee: Becton, Dickinson and Company, Franklin Lakes, N.J.

[21] Appl. No.: 443,233

[22] Filed: May 17, 1995

Related U.S. Application Data

[62] Division of Ser. No. 231,544, Apr. 22, 1994.

[51] Int. Cl.$^6$ .............. B01D 17/00; B01D 21/26
[52] U.S. Cl. .............. 210/513; 210/511; 252/60; 252/315.01; 252/315.1; 435/2; 514/944
[58] Field of Search .............. 210/511, 513, 210/516; 435/1, 2; 514/944; 252/60, 315.01, 315.1

[56] References Cited

U.S. PATENT DOCUMENTS

| | | | |
|---|---|---|---|
| 4,910,015 | 3/1990 | Sung et al. | 424/78 |
| 5,093,019 | 3/1992 | Tagawa et al. | 210/516 |
| 5,252,340 | 10/1993 | Honeycutt | 424/489 |
| 5,266,304 | 11/1993 | Baffelli et al. | 424/49 |

*Primary Examiner*—John Kim
*Attorney, Agent, or Firm*—Nanette S. Thomas

[57] ABSTRACT

A blood collection assembly with gel formulations including a polydimethylsiloxane-polyethyleneoxide copolymer gelled with dibenzylidine sorbitol in the presence of water or alcohol. The gel formulations are useful for facilitating the separation of blood serum or plasma from the cellular portion of blood or as a thermoreversible shear sensitive substance.

1 Claim, 1 Drawing Sheet

BLOOD COLLECTION ASSEMBLY WITH BLOOD COMPATIBLE, SHEAR SENSITIVE GELS

This is a divisional of co-pending application Ser. No. 08/231,544, filed Apr. 22, 1994.

BACKGROUND OF THE INVENTION

1. Field of the Invention

This invention relates to gel formulations that are blood compatible and shear sensitive. More particularly, such gel formulations comprising a polydimethylsiloxane-polyethyleneoxide copolymer gelled with dibenzylidine sorbitol in the presence of water or alcohol, are particularly useful for facilitating the separation of blood serum or plasma from the cellular portion of blood or as a thermoreversible shear-sensitive substance for use in mechanical serum separation devices.

2. Description of Related Art

Biochemical tests carried out in a clinical laboratory require use of blood serum or plasma as a sample. For preparing the sample for examination, it is frequently necessary to separate the blood serum or plasma from the solid blood components. There are known various types of blood separating compositions which are used to separate the blood components from one another.

Some blood separating compositions are formulated into thixotropic gels. For example, fumed silica to crosslink polar polyester or fatty oils into a gel or fumed silica to form a reversibly-formed network of silica particles to gel nonpolar oils.

U.S. Pat. Nos. 3,852,194, 3,920,549 and 3,997,442 disclose dibenzylidene sorbitol (DBS) gels of hydrocarbon or silicone oils that have an opaque characteristic. DBS is a gelling agent that is capable of forming a molecular network. Unlike the thixotropic gels, DBS gels of hydrocarbon or silicone oils loose all structural integrity under stress, liquefy under centrifugation, and do not reform into a solid gel. Consequently, these gels are not adequate for separating blood into liquid and solid components.

Furthermore, use of hydrophobic hydrocarbon or silicone oils in blood collection tubes is problematic. As disclosed in U.S. Pat. No. 5,247,633, blood components such as cells and fibrin clots adhere tenaciously to non-water wettable surfaces. Therefore, when the inside walls of blood collection tubes become coated with the hydrocarbon or silicone type oils of these gels, cells and clot debris will adhere, preventing clean separation of liquid and solid components of blood. Therefore, hydrocarbon and silicone type oils are not blood compatible in blood collection applications.

Whereas there are numerous publications related to gelled silicones, hydrocarbons, and polyesters there are no publications that suggest or teach that polymers containing polar ethyleneoxide moieties can be gelled with dibenzylidine sorbitol (DBS) in the presence of polar liquids yielding gels that will flow under shear forces involved in centrifugation, will not liquefy under shear, are readily gelled using water or alcohol and are compatible in blood collection applications.

SUMMARY OF THE INVENTION

The present invention is gel formulations comprising (a) a block copolymer; and (b) a gelling agent. Most desirably, gel formulations of the present invention comprise (a) a block copolymer, (b) a gelling agent; and (c) a liquid vehicle.

Preferably, gel formulations of the present invention comprise polydimethylsiloxane-polyethyleneoxide (PDMS/PEO) copolymers gelled with dibenzylidine sorbitol (DBS) in the presence of water or alcohols.

Most preferably, the gel formulations comprise:

(a) from about 50 to about 100% by weight of PDMS/PEO;

(b) from about 0.01 to about 10% by weight of DBS; and (c) from about 0 to about 50% by weight of water or alcohol.

The gelation of oils containing water soluble moieties such as polyethyleneoxide (PEO) has not been reported and the formation of gels in the presence of water or alcohols is a surprising discovery, The gel formulations of the present invention are useful as thermoreversible shear-sensitive substances for use in mechanical serum devices and for facilitating the separation of blood serum or plasma from the cellular portion of blood when used in blood collection tubes.

Attributes of the gel formulations of the present invention include thermoreversibility properties in that the gel can be heated to a viscous liquid state that returns to gel on cooling, retaining a substantially clear appearance and the ability to flow under shear forces involved in centrifugation. Consequently, gel formulations of the present invention do not irreversibly liquify under certain shear forces and exhibit thixotropic-like behavior and therefore may be useful as serum separation gels in blood collection applications.

Another attribute of the gel formulations of the present invention includes its use as an electrophoresis, for example in drug delivery. Water containing gels, such as PDMS/PEO, may exhibit electrical conductivity and permit inclusion of mobile electrolytes into the gel.

Another advantage of the gel formations of the present invention include its ability to maintain uniform physical and chemical properties for extended periods of time prior to use, as well as during transportation and processing of blood samples. Therefore, the components of the gel formulation will not separate under normal storage and/or use.

Most notably, the gel formulations of the present invention readily form a stable portion under normal centrifugation conditions and are relatively inert or unreactive toward the substances in the blood whose presence or concentration is to be determined. Therefore the gel formulations of the present invention are blood compatible and can be readily used in blood collection applications. As compared to hydrocarbon or silicone type oils that are typically used in blood collection applications, the gel formulations of the present invention will not attract cells and clot debris that is in blood specimens.

The gel formulations of the present invention also are thixotropic or exhibit thixotropic like properties in that the gel formulation will flow under radial stress imposed during centrifugation of blood. When used in a blood collection tube, the flowing gel reforms into a solid barrier that mechanically separates solid and liquid blood components on the basis of density when centrifugation is ceased. Since deformation of a solid barrier is essential to blood separation that resists inadvertent mechanical remixing as might occur during transport or storage of blood specimen the gel formulations of the present invention are acceptable for use in blood collection applications.

Furthermore, a desirable chemical characteristic of the gel formulations of the present invention is that it may be formed in the presence of water or alcohol to modify gel performance, such as specific gravity. A desirable physical characteristic of gel formulations of the present invention is its water white appearance.

DETAILED DESCRIPTION

Figure 1:
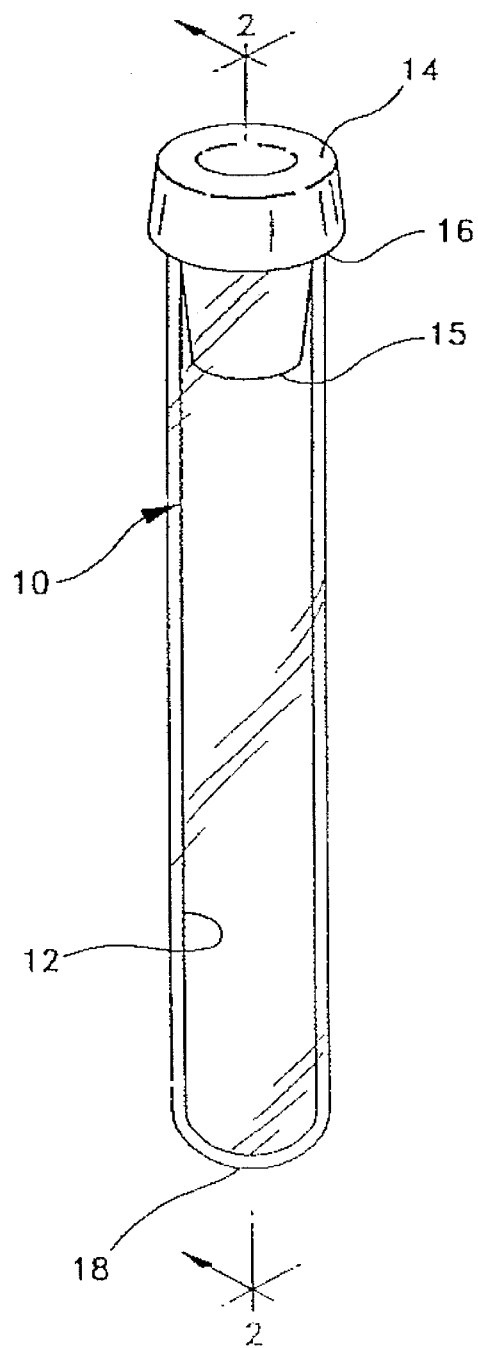
FIG. 1 is a perspective view of a typical blood collection tube with a stopper.

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The gel formulations of the present invention preferably comprise a block copolymer; and a gelling agent. The gel formulations of the present invention most preferably, further comprise a liquid vehicle.

Most preferably, the block copolymer of the present invention is polydimethylsiloxane-polyethylene oxide (PDMS/PEO). PDMS/PEO is commercially available as SILWET® surfactant (trademark of Union Carbide, 39 Old Ridgebury Road, Danbury, Conn. 06817-0001).

SILWET surfactants are chemically unique and should not be confused with conventional polydimethylsiloxanes because they are composed of a siloxane backbone with organic polyalkyleneoxide pendants, forming chemical structures whose variations provide a wide range of useful performance characteristics.

SILWET surfactants are nonionic, concentrated, and function in aqueous and nonaqueous systems. SILWET surfactants comprise the following features: low surface tension; high wetting; good dispersing, emulsifying, lubricity; sheen, gloss enhancing; static suppressing; contribute to antifoaming; moderate profoaming; broad range of solubility and aqueous cloud points; low volatility, good thermal stability; compatible with organic surfactants and system components, and low toxicity.

SILWET surfactants are polyalkylene oxide—modified polydimethylsiloxanes. These block copolymers are of two distinct structural types. The major class is a linear polydimethylsiloxane to which polyethers have been grafted through a hydrosilation reaction. This process results in an alkyl-pendant (AP type) copolymer, in which the polyalkylene oxide groups are attached along the siloxane backbone through a series of hydrolytically stable Si—C bonds. They have the following general formula:

$$Me_3SiO(Me_2SiO)_x(MeSiO)_ySiMe_3$$
$$|$$
$$PE$$

where $PE = -CH_2CH_2CH_2O(EO)_m(PO)_nZ$

In this formula, Me represents methyl, EO represents ethyleneoxy, PO represents 1,2-propyleneoxy, and Z can be either hydrogen or a lower alkyl radical.

The other class is a branched polydimethylsiloxane to which polyesters have been attached through condensation chemistry. This creates an alkoxy-end-blocked (AEB Type) copolymer, in which the polyalkylene oxide groups are attached at the ends of the silicone backbone through Si—O—C bonds. This linkage offers limited resistance to hydrolysis under neutral or slightly alkaline conditions, but breaks down quickly in acidic environments. They have the general formula:

$$(MeSi)_{y-2}[(OSiMe_2)_{x/y}O-PE]_y$$
$$|$$
$$PE$$

where $PE = -(EO)_m(PO)_nR$ and R represents a lower alkyl group.

By varying the coefficients x, y, m, and n, a broad range of SILWET surfactants are produced. These surfactants offer unique properties and performance that are not readily achievable with conventional organic surfactants.

Particular SILWET surfactants that are useful in the gel formulations of the present invention include, but are not limited to, L720, L722 and L7500.

Most preferably, a SILWET surfactant is present in the gel formulation in an amount from about 50 to about 99.9% by weight and most preferably at about 90% per weight.

Most preferably the gelling agent of the present invention is dibenzylidene sorbitol (DBS). Since DBS is able to form a molecular network it can be successfully used to gel polydimethyl siloxane/polyethylene oxide block copolymer oils.

It is taught that DBS can be used to clarify plastics as well as to gel hydrophobic solvents and oils. The function of DBS in clarification of plastics is thought to be due to formation of small crystallites which do not scatter light as efficiently as larger crystallites, therefore yielding improved clarity.

Gel formation of oils containing polar moieties such as polyethylereoxide (PEO) in the presence of polar solvents such as water or alcohol is surprising because one skilled in the art would believe that the self association of DBS would be inhibited by competitive hydrogen bonding with polar groups. It is believed that the formation of gels of the present invention is due to the formation of a molecular network within the fluid phase induced by self association through hydrogen bonding.

Dibenzylidine sorbitol (DBS) is present in the gel formulations in an amount from about 0.01 to about 10% by weight and most preferably at about 0.25% by weight.

Optionally, a satisfactory liquid vehicle is used for admixture of the components. A satisfactory liquid vehicle such as water or alcohol may be selected. Preferably, the alcohol is selected from simple aliphatic alcohols such as methyl, ethyl or propyl alcohol, but is not limited to short chain length alcohols.

If water is used in the gel formulations, it is present in an amount from about 0 to about 50% by weight and most preferably at about 10% by weight.

If alcohol is used in the gel formulations, it is present in an amount from about 0 to about 50% by weight and most preferably at about 10% by weight.

The specific gravity of the gel formulations can be controlled by the surfactant, final concentration of DBS and any added water or alcohol.

Most preferably, the gel formulations of the present invention may be used in blood collection applications. Most notably, in blood collection tubes.

Referring to the drawings in which like reference characters refer to like parts throughout the several views thereof, FIG. 1 shows a typical blood collection tube 10, having an open end 16, a closed end 18 and a stopper 14 that includes a lower annular portion or skirt 15 which extends into and presses against the inside wall 12 of the tube for maintaining stopper 14 in place.

Figure 2:
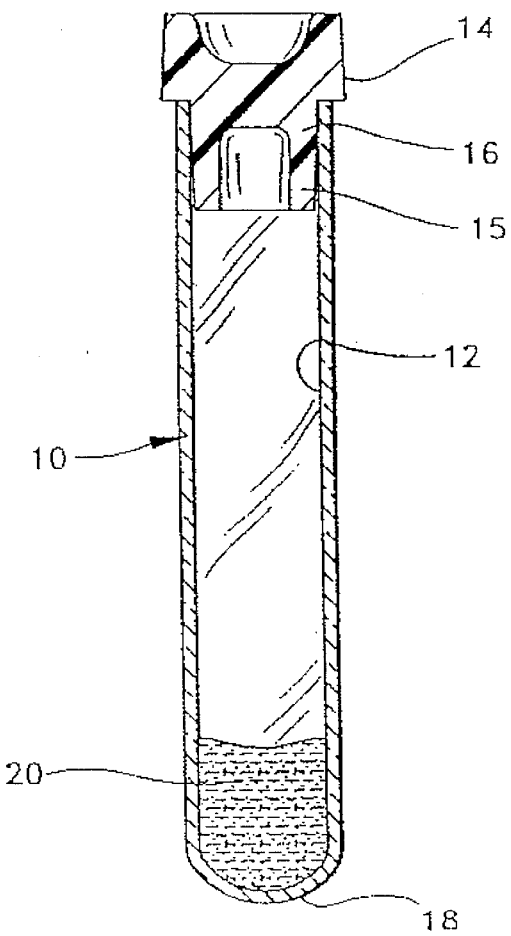
FIG. 2 is a longitudinal sectional view of the tube of FIG. 1, taken along line 2—2, comprising a gel formulation of the present invention.

FIG. 2 shows the use of the gel formulations of the present invention in a typical blood collection tube. A gel formulation 20 is shown at the closed end of the tube.

A blood sample of interest can be transferred into tube 10 that comprises gel formulation 20. Tube 10 is then placed in a centrifuge and subjected to centrifugal force. This causes the gel formulation 20 to move to a point dividing the heavier and lighter fractions of the sample.

Various other modifications will be apparent to and may be readily made by those skilled in the art without departing from the scope and spirit of the invention.

The examples are not limited to any specific embodiment of the invention, but are only exemplary.

EXAMPLE I

GEL FORMATION OF PDMS-PEO COMPOSITIONS WITH WATER

Four different formulations of a water-soluble PEO-PDMS copolymer surfactant, SILWET surfactant L720, having a specific gravity of 1.04, DBS and water were mixed in glass test tubes. The tubes were heated in a sand bath held at 175°–200° C. or with a heat gun with occasional mixing while avoiding wholesale boiling. DBS was apparently soluble in certain compositions as evidenced by the disappearance of suspended particles. Full DBS solubility was not observed for other compositions.

The tubes were capped and allowed to cool in an inclined test-tube rack to form gels with a slant. Gel formation was noted by resistance to flow on tube inversion. Most compositions showed gel formation within a few hours whereas others required up to 48 hours to fully gel. Table I lists the results obtained.

TABLE I

| | | L720 Gels | | |
|---|---|---|---|---|
| Wt. % DBS in L720 | Neat L720 | 90% L720 10% Water | 75% L720 25% Water | 50% L720 50% Water |
| 0.25 | (−) | (−) | (−) | (+) |
| 0.5 | (+) | (−) | (+) | (+) |
| 0.75 | (+) | (+) | (+) | (+) |
| 1.0 | (+), PI | (+), PI | (+), PI | (+), PI |

(−) = no gel formed, (+) = gel formed, PI = DBS partially insoluble

EXAMPLE II

GEL FORMATION OF PDMS-PEO COMPOSITIONS WITH ISOPROPANOL

Four different formulations of an alcohol soluble (but water insoluble) PEO-PDMS copolymer surfactant, SILWET surfactant L722, having a specific gravity of 0.99, DBS and isopropanol were mixed in glass test tubes. The tubes were heated in a sand bath held at 175°–200° C. or with a heat gun with occasional mixing while avoiding wholesale boiling. DBS was apparently soluble in certain compositions as evidenced by the disappearance of suspended particles. Full DBS solubility was not observed for other compositions.

The tubes were capped and allowed to cool in an inclined test-tube rack to form gels with a slant. Gel formation was noted by resistance to flow on tube inversion. Most compositions showed gel formation within a few hours whereas others required up to 48 hours to fully gel. Table II lists the results obtained.

TABLE II

| | | L722 Gels | | |
|---|---|---|---|---|
| Wt. % DBS in L722 | Neat L722 | 90% L722 10% Alcohol | 75% L722 25% Alcohol | 50% L722 50% Alcohol |
| 0.25 | (+) | (+), PI | (+) | (+), PI |
| 0.5 | (+) | (+), PI | (+), PI | (+), PI |
| 0.75 | (−) | (+), I | (+) | (+), W |
| 1.0 | (−) | (+), W | (+) | (+), W |

(−) = no gel formed, (+) = gel formed, PI = DBS partially insoluble, W = white gel

EXAMPLE III

GEL FORMATION OF PDMS-PEO COMPOSITIONS WITH ISOPROPANOL

Four different formulations of an alcohol soluble (but water insoluble) PEO-PDMS copolymer surfactant, SILWET surfactant L7500, having a specific gravity of 0.99, DBS and isopropanol were mixed in glass test tubes. The tubes were heated in a sand bath held at 175°–200° C. or with a heat gun with occasional mixing while avoiding wholesale boiling. DBS was apparently soluble in certain compositions as evidenced by the disappearance of suspended particles. Full DBS solubility was not observed for other compositions.

The tubes were capped and allowed to cool in an inclined test-tube rack to form gels with a slant. Gel formation was noted by resistance to flow on tube inversion. Most compositions showed gel formation within a few hours whereas others required up to 48 hours to fully gel Table III lists the results obtained.

TABLE III

| | | L7500 Gels | | |
|---|---|---|---|---|
| Wt. % DBS in L7500 | Neat L7500 | 90% L7500 10% Alcohol | 75% L7500 25% Alcohol | 50% L7500 50% Alcohol |
| 0.25 | (+) | (+), PI | (+) | (+), PI |
| 0.5 | (+) | (+), PI | (+) | (+), W |
| 0.75 | (−) | (+), W | (+) | (+) |
| 1.0 | (−) | (+), W | (+), W | (+), W |

(−) = no gel formed, (+) = gel formed, PI = DBS partially insoluble, W = white gel

EXAMPLE IV

GEL FORMATION OF PDMS-PEO COMPOSITIONS WITH ISOPROPANOL

Four different formulations of an alcohol soluble (but water insoluble) PEO-PDMS copolymer surfactant, SILWET surfactant L77, having a specific gravity of 0.99, DBS and isopropanol were mixed in glass test tubes. The tubes were heated in a sand bath held at 175°–200° C. or with a heat gun with occasional mixing while avoiding wholesale boiling. DBS was apparently soluble in certain compositions as evidenced by the disappearance of suspended particles. Full DBS solubility was not observed for other compositions.

The tubes were capped and allowed to cool in an inclined test-tube rack to form gels with a slant. Gel formation was noted by resistance to flow on tube inversion. Most compositions showed gel formation within a few hours whereas others required up to 48 hours to fully gel. Table IV lists the results obtained.

TABLE IV

| | L77 Gels | | | |
|---|---|---|---|---|
| Wt. % DBS in L77 | Neat L77 | 90% L77 10% Alcohol | 75% L77 25% Alcohol | 50% L77 50% Alcohol |
| 0.25 | (−) | — | — | (−) |
| 0.5 | (+) | (−) | (−) | (+) |
| 0.75 | — | (+) | (+) | (+) |
| 1.0 | — | — | — | — |

(−) = no gel formed, (+) = gel formed, PI = DBS partially insoluble, W = white gel

EXAMPLE V

GEL FORMATION OF PDMS-PEO COMPOSITIONS WITH ISOPROPANOL

Four different formulations of an alcohol soluble (but water insoluble) PEO-PDMS copolymer surfactant, SIL-WET surfactant L7001, having a specific gravity of 0.99, DBS and isopropanol were mixed in glass test tubes. The tubes were heated in a sand bath held at 175°–200° C. or with a heat gun with occasional mixing while avoiding wholesale boiling. DBS was apparently soluble in certain compositions as evidenced by the disappearance of suspended particles. Full DBS solubility was not observed for other compositions.

The tubes were capped and allowed to cool in an inclined test-tube rack to form gels with a slant. Gel formation was noted by resistance to flow on tube inversion. Most compositions showed gel formation within a few hours whereas others required up to 48 hours to fully gel. Table V lists the results obtained.

TABLE V

| | L7001 Gels | | | |
|---|---|---|---|---|
| Wt. % DBS in L7001 | Neat L7001 | 90% L7001 10% Alcohol | 75% L7001 25% Alcohol | 50% L7001 50% Alcohol |
| 0.25 | (−) | (−) | (−) | (+) |
| 0.5 | (+) | (+) | (+) | (+) |
| 0.75 | (+) | (+) | (+) | (+), PI |

TABLE V-continued

| | L7001 Gels | | | |
|---|---|---|---|---|
| Wt. % DBS in L7001 | Neat L7001 | 90% L7001 10% Alcohol | 75% L7001 25% Alcohol | 50% L7001 50% Alcohol |
| 1.0 | — | — | — | — |

(−) = no gel formed, (+) = gel formed, PI = DBS partially insoluble

EXAMPLE VI

THIXOTROPIC BEHAVIOR OF PDMS-PEO GELS COMPARISON OF GEL FORMATIONS WITH WATER AS COMPARED TO GEL FORMATIONS WITH ALCOHOL

Gels formed from L720 were compared to gels of L722, L7500 and L7001. A single preparation of L720 gel was made in the proportion of 0.75 wt.% DBS and 75/25 L720 and water mixture, as listed in Table I. L722 gels were made in the proportion of 50/50 mixtures of surfactant and isopropanol at 0.25, 0.5, and 0.75 wt. % DBS, as listed in Table II. A single preparation of gel was made in the proportion of 0.75% wt. % DBS and 75/25 L7500 and isopropanol, as listed in Table III. L7001 gels were prepared as listed in Table V.

Gel slants were formed in glass tubes as described in Example I and citrated whole porcine blood was added to each tube. Blood was recalcified with 200 μL of 0.2M $CaCl_2$ per ml of blood and allowed to clot for 15 minutes while continuously rotating on a standard inverting hematology mixer after which the tube was centrifuged for 10 minutes in a fixed rotor hematology centrifuge. Upon centrifugation, L722 and L7500 gels migrated to the serum-air interface and L7001 gels migrated to the serum-cell interface. By contrast, the more dense L720 gel did not migrate on centrifugation and remained at the bottom of the tube.

What is claimed is:

1. A blood collection assembly comprising a blood collection container having an open end, a closed end, a stopper for closing said open end and a gel formulation in said container comprising a block copolymer of polydimethyl siloxane/polyethylene oxide copolymer, a gelling agent of dibenzylidene sorbitol and a liquid vehicle of water or alcohol.

* * * * *